United States Patent [19]

Beschke et al.

[11] 4,147,874

[45] Apr. 3, 1979

[54] PROCESS FOR THE PRODUCTION OF PYRIDINE AND 3-METHYL PYRIDINE

[75] Inventors: Helmut Beschke; Heinz Friedrich, both of Hanau, Fed. Rep. of Germany

[73] Assignee: Deutsche Gold- und Silber Scheideanstalt vormals Roessler, Frankfurt, Fed. Rep. of Germany

[21] Appl. No.: 871,976

[22] Filed: Jan. 24, 1978

[30] Foreign Application Priority Data

Jan. 26, 1977 [DE] Fed. Rep. of Germany ....... 2703049

[51] Int. Cl.$^2$ ............................................. C07D 213/12
[52] U.S. Cl. ..................................................... 546/251
[58] Field of Search ..................................... 260/290 P

[56] References Cited

FOREIGN PATENT DOCUMENTS 6512937  4/1966  Netherlands .......................... 260/290 P
1005984  9/1965  United Kingdom .................. 260/290 P

OTHER PUBLICATIONS

Emmett, Catalysis, Vol. VII, Reinhold Pub., pp. 5–9 (1960).

*Primary Examiner*—Alan L. Rotman
*Attorney, Agent, or Firm*—Cushman, Darby & Cushman

[57] ABSTRACT

Pyridine and 3-methyl pyridine are produced by the catalytic reaction of acrolein and acetaldehyde with ammonia in the gas phase. There is used as the catalyst a highly dispersed aluminum silicate containing 3 to 30 weight percent aluminum oxide, a BET surface area of 200 to 800 m$^2$/g, a pore volume of 0.4 to 1.0 cm$^3$/g and a pore diameter of 20 to 100 × 10$^{-8}$ cm.

19 Claims, No Drawings

PROCESS FOR THE PRODUCTION OF PYRIDINE AND 3-METHYL PYRIDINE

BACKGROUND OF THE INVENTION

The invention is directed to a process for the production of pyridine and 3-methyl pyridine by catalytic reaction of acrolein and acetaldehyde with ammonia in the gas phase.

It is known that in the reaction of acrolein with ammonia in the gas phase in the presence of catalysts pyridine and 3-methyl pyridine are formed. As catalysts there have been especially used compounds of the elements Al, F and O which additionally contain at least one element of the second, third or fourth groups of the periodic system and which have been treated with oxygen at temperatures of 550° to 1200° C. (German Offenlegungsschrift No. 2,151,417 or corresponding Beschke U.S. Pat. No. 3,898,177) or at least two elements of the second, fourth, fifth or sixth groups of the periodic system (German OS 2,224,160 or corresponding Beschke U.S. Pat. No. 3,960,766), or at least one element of the second main group of the periodic system (German OS 2,239,801 or corresponding Beschke U.S. Pat. No. 3,917,542). It is also known to carry out the reaction in a fluidized bed with the acrolein fed in separately from the ammonia (German OS 2,449,340 and corresponding Beschke U.S. application No. 622,488 filed Oct. 15, 1975). The disadvantage of these processes is that it is not possible to produce pyridine and 3-methyl pyridine in a substantially different molar ratio than 1 to 2.

Furthermore, it is known that the molar ratio of pyridine to 3-methyl pyridine can be adjusted in a wide range at random by varying the ratio of acrolein to acetaldehyde. As catalysts there are used aluminum oxide, silica or their mixtures, in a given case with addition of oxides of additional elements (Hargrave British Pat. No. 963,887) and in a given case containing fluorides (Distillers Netherlands published application No. 6512937) or there can be used as catalysts compounds consisting of B, P and O, in a given case on carriers of aluminum oxide, silica or their mixtures (Campbell British Pat. No. 1,005,984). In these processes the space-time-yields of pyridine and 3-methyl pyridine are small.

SUMMARY OF THE INVENTION

There has now been found a process for the production of pyridine and 3-methyl pyridine by catalytic reaction of acrolein and acetaldehyde with ammonia in the gas phase which is characterized by using as the catalyst highly dispersed aluminum silicate which contains 3 to 30 weight percent aluminum oxide, a BET surface area of 200 to 800 m$^2$/g, a pore volume of 0.4 to 1.0 cm$^3$/g and a pore diameter of 20 to 100 $\times 10^{-8}$ cm (20 to 100 A). With this process there are produced molar ratios of pyridine to 3-methyl pyridine varying from about 2:1 to 1:2 and there are obtained high space-time-yields.

The aluminum silicates used according to the invention preferably have an aluminum oxide content of 5 to 20% and especially from 10 to 15%. They preferably have a BET surface area of 300 to 600 m$^2$/g, a pore volume of 0.6 to 0.8 cm$^3$/g and a pore diameter of 40 to 80$\times 10^{-8}$ cm.

The aluminum silicates can be made in known manner, for example, by treating an aqueous sodium silicate solution with sulfuric acid and mixing the silica gel produced with aluminum sulfate and ammonia, separating and freeing of the aluminum silicate from foreign ions, drying and tempering (Paul H. Emmett, Catalysis, Vol. VII, Reinhold Publishing Corp., especially pages 5 to 9). The entire disclosure of Emmett is hereby incorporated by reference and relied upon.

To carry out the process of the invention acrolein, acetaldehyde and ammonia are added in customary manner in gaseous form. The molar proportions can be chosen substantially at random. However, it is generally suitable per mole of acrolein to use about 0.1 to 1.0 mole, preferably 0.2 to 0.8 mole, particularly 0.4 to 0.6 mole of acetaldehyde. Besides it is generally suitable to add per mole of aldehyde (acrolein and acetaldehyde) at least about 1 mole of ammonia. It is advantageous to use per mole of aldehyde about 1.0 to 3.0 moles, especially 1.3 to 2.5 moles, of ammonia. Suitably there is introduced additionally an inert gas, especially nitrogen, that is, advantageously per mole of aldehyde 0.5 to 3.0 moles, particularly 1.0 to 2.5 moles, of inert gas.

Whether the formation of pyridine or 3-methyl pyridine is favored depends to a certain extent on the molar ratio of acetaldehyde to acrolein. The greater is the molar ratio the greater in general is the proportion of pyridine.

The catalyst is used in a fixed bed, generally in a particle size of 0.2 to 3.0 mm, especially of 0.5 to 2.0 mm, or preferably in a fluidized bed, generally in a particle size of 0.1 to 3.0 mm, especially of 0.2 to 2.0 mm. Advantageously the aldehydes are fed into the reaction space separately from the ammonia. Particularly there is chosen for this purpose the procedure of German OS 2,449,340 or corresponding Beschke U.S. application No. 622,488 filed Oct. 15, 1975, however, with the difference that instead of acrolein in each case there is added a mixture of acrolein and acetaldehyde. There are hereby incorporated by reference and relied upon the entire disclosures of German OS 2,449,340 and Beschke U.S. application No. 622,488.

The reaction takes place at temperatures between about 300° and 500° C., especially between 380° and 480° C. The pressure can be chosen substantially at random, however, it is recommended so that a simple apparatus can be used to operate at normal pressure or only moderately lowered or elevated pressure up to about 3 bar. A slight under pressure or over pressure results in a given case in that the gases are sucked through the plant or forced through by pressure.

The process can comprise, consist essentially of or consist of the steps set forth and the materials employed can comprise, consist essentially of or consist of those set forth.

Unless otherwise indicated all parts and percentages are by weight.

DESCRIPTION OF THE PREFERRED EMBODIMENTS

EXAMPLE 1

There was used a fluidized bed reactor. This consisted of a tube 70 mm wide which had a free space in its lower portion 200 mm high; thereover at intervals of 50 mm there were 40 wire screens each having an interval between meshes of 5 mm and there was provided above a free space having a height of 600 mm and a width of up to 160 mm.

There were lead into the reactor in gaseous form in uniform flow hourly from below a gas mixture of 1875 normal liters (i.e., measured at standard temperature and pressure) of nitrogen and 2690 normal liters of ammonia and from the side there were led into the fluidized bed 130 mm above the bottom of the reactor a gaseous mixture of 2100 grams of acrolein, 990 grams of acetaldehyde and 260 normal liters of nitrogen.

The reactor contained 2.0 kg of catalyst. The catalyst consisted of aluminum silicate containing 13% $Al_2O_3$, had a BET surface area of 500 cm$^2$/g, a pore volume of 0.75 cm$^3$/g, a pore diameter of $60 \times 10^{-8}$ cm (i.e., 60 A) and a particle size of 0.4 to 1.0 mm.

The temperature in the reactor was held at 440° C. The reaction mixture which left the reactor was free from acrolein and acetaldehyde. It was led at a temperature of 250° C. into a gas washing apparatus in which the pyridine compounds formed were washed out by means of water. The remaining residual gas of ammonia and nitrogen after addition of 950 normal liters of ammonia hourly were recycled into the reactor.

The reaction of acrolein and acetaldehyde was 100%. There were produced hourly 796 grams of pyridine and 803 grams of 3-methyl pyridine, corresponding to a molar ratio of 1.2 to 1 and a yield of 27% and 46% based on the acrolein added. Besides there were obtained 90 grams of 2-methyl pyridine. Per kg of catalyst per hour there was a yield of pyridine and 3-methyl pyridine of 800 grams.

EXAMPLE 2

The procedure was the same as in Example 1 but there were fed in hourly 1683 grams of acrolein and 1322 grams of acetaldehyde. The yield per hour was 644 grams of pyridine and 533 grams of 3-methyl pyridine, corresponding to a molar ratio of 1.4 to 1.0 and a yield of 27 and 38% based on the acrolein added. Besides there were obtained 78 grams of 2-methyl pyridine. Per kg of catalyst per hour the yield of pyridine and 3-methyl pyridine was 588 grams.

EXAMPLE 3

The procedure was the same as in Example 1 but there were fed in hourly 1795 grams of acrolein and 1233 grams of acetaldehyde. There were obtained hourly 688 grams of pyridine and 651 grams of 3-methyl pyridine, corresponding to a molar ratio of 1.3 to 1.0 and a yield of 27 and 44% based on the acrolein added. Besides there were obtained 83 grams of 2-methyl pyridine. Per kg of catalyst per hour the yield of pyridine and 3-methyl pyridine was 670 grams.

EXAMPLE 4

The procedure was the same as in Example 1 but there were fed in hourly 2357 grams of acrolein and 793 grams of acetaldehyde. There were obtained hourly 700 grams of pyridine and 798 grams of 3-methyl pyridine, corresponding to a molar ratio of 1 to 1 and a yield of 40 and 42% based on the acrolein added. Besides there were obtained 88 grams of 2-methyl pyridine. Per kg of catalyst per hour the yield of pyridine and 3-methyl pyridine was 749 grams.

What is claimed is:

1. In a process for the production of pyridine and 3-methyl pyridine by the catalytic reaction of acrolein and acetaldehyde with ammonia in the gas phase the improvement consisting essentially of employing a gaseous mixture consisting essentially of (1) acetaldehyde, acrolein and ammonia or (2) acetaldehyde, acrolein, ammonia and an inert gas and employing as the catalyst a catalyst consisting essentially of highly dispersed aluminum silicate containing 3 to 30 weight percent aluminum oxide, a BET surface area of 200 to 800 m$^2$/g, a pore volume of 0.4 to 1.0 cm$^3$/g and a pore diameter of 20 to $100 \times 10^{-8}$ cm.

2. A process according to claim 1 wherein the catalyst is employed in a fluidized bed and the acrolein and acetaldehyde are introduced into the reactor separately from the ammonia.

3. A process according to claim 2 wherein the catalyst has an aluminum oxide content of 5 to 20 weight percent, a BET surface area of 300 to 600 m$^2$/g, a pore volume of 0.6 to 0.8 cm$^3$/g and a pore diameter of 40 to $80 \times 10^{-8}$ cm.

4. A process according to claim 3 wherein the aluminum oxide content is 10 to 15 weight percent.

5. A process according to claim 4 wherein per mole of acrolein there is employed 0.4 to 0.6 mole of acetaldehyde and per mole of total aldehyde 1.3 to 2.5 moles of ammonia.

6. A process according to claim 5 wherein there is also employed 1.0 to 2.5 moles of inert gas per mole of total aldehyde.

7. A process according to claim 3 wherein per mole of acrolein there is employed 0.4 to 0.6 mole of acetaldehyde and per mole of total aldehyde 1.3 to 2.5 moles of ammonia.

8. A process according to claim 7 wherein there is also employed 1.0 to 2.5 moles of inert gas per mole of total aldehyde.

9. A process according to claim 3 wherein per mole of acrolein there is employed 0.2 to 0.8 mole of acetaldehyde and per mole of total aldehyde 1.0 to 3.0 moles of ammonia.

10. A process according to claim 9 wherein there is also employed 0.5 to 3.0 moles of inert gas per mole of total aldehyde.

11. A process according to claim 2 wherein there is employed per mole of acrolein 0.4 to 0.6 mole of acetaldehyde.

12. A process according to claim 11 wherein there is employed per mole of total aldehyde 1.3 to 2.5 moles of ammonia.

13. A process according to claim 12 wherein there is also employed 1.0 to 2.5 moles of inert gas per mole of total aldehyde.

14. A process according to claim 2 wherein there is employed per mole of acrolein 0.2 to 0.8 mole of acetaldehyde and per mole of total aldehyde 1.0 to 3.0 moles of ammonia.

15. A process according to claim 14 wherein there is also employed 0.5 to 3.0 moles of inert gas per mole of total aldehyde.

16. A process according to claim 15 wherein the catalyst is employed in a fluidized bed and the acrolein and acetaldehyde are introduced into the reactor separately from the ammonia.

17. A process according to claim 2 wherein there is employed per mole of acrolein 0.1 to 1.0 mole of acetaldehyde and at least 1 mole of ammonia per mole of total aldehyde.

18. A process according to claim 2 wherein the gaseous mixture consists of (1) acetaldehyde, acrolein and ammonia or (2) acetaldehyde, acrolein, ammonia and an inert gas and the catalyst consists of said highly dispersed aluminum silicate.

19. A process according to claim 18 wherein there is employed 0.4 to 0.6 mole of acetaldehyde per mole of acrolein and 1.3 to 2.5 moles of ammonia per mole of total aldehyde and there is employed 0.5 to 3.0 mole of inert gas per mole of total aldehyde.

* * * * *